(12) United States Patent
Mehta et al.

(10) Patent No.: US 9,637,798 B2
(45) Date of Patent: May 2, 2017

(54) GENETIC SIGNATURE OF VULNERABILITY TO INHIBITORS OF BASE EXCISION REPAIR (BER) IN CANCER

(71) Applicant: Dignity Health, Phoenix, AZ (US)

(72) Inventors: Shwetal V. Mehta, Chandler, AZ (US); Michael E. Berens, Phoenix, AZ (US); Harshil Dineshkumar Dhruv, Tempe, AZ (US)

(73) Assignees: Dignity Health, San Francisco, CA (US); The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 14/890,685

(22) PCT Filed: May 21, 2014

(86) PCT No.: PCT/US2014/039033
§ 371 (c)(1),
(2) Date: Nov. 12, 2015

(87) PCT Pub. No.: WO2014/190090
PCT Pub. Date: Nov. 27, 2014

(65) Prior Publication Data
US 2016/0102360 A1    Apr. 14, 2016

Related U.S. Application Data

(60) Provisional application No. 61/825,962, filed on May 21, 2013.

(51) Int. Cl.
| | | |
|---|---|---|
| *A01N 43/52* | (2006.01) | |
| *C12Q 1/68* | (2006.01) | |
| *A61K 31/131* | (2006.01) | |
| *A61K 31/495* | (2006.01) | |

(52) U.S. Cl.
CPC .......... *C12Q 1/6886* (2013.01); *A61K 31/131* (2013.01); *A61K 31/495* (2013.01); *C12Q 2565/501* (2013.01); *C12Q 2600/106* (2013.01); *C12Q 2600/158* (2013.01); *C12Q 2600/16* (2013.01)

(58) Field of Classification Search
CPC ................................... C12Q 1/6886
USPC ....................................................... 514/393
See application file for complete search history.

(56) References Cited

U.S. PATENT DOCUMENTS

| | | | |
|---|---|---|---|
| 8,043,807 B2 * | 10/2011 | Livneh | C12Q 1/6886 435/6.1 |
| 8,324,282 B2 | 12/2012 | Gerson et al. | |
| 2008/0279961 A1 | 11/2008 | Burger | |
| 2010/0209920 A1 | 8/2010 | Baker et al. | |
| 2013/0030237 A1 | 1/2013 | Theuer | |
| 2013/0123566 A1 * | 5/2013 | Lupold | A61K 31/7105 600/1 |

FOREIGN PATENT DOCUMENTS

| | | |
|---|---|---|
| WO | 2011058367 A2 | 5/2011 |
| WO | 2011058367 A3 | 8/2011 |
| WO | 2014190090 A1 | 11/2014 |

OTHER PUBLICATIONS

Yan et al. Clin Cancer Res20 07;13(5)Mar. 1, 2007, 1532-1539.*
Tang et al. Neuro-Oncology 13(5):471-486, 2011.*
Mohan, Chapter 19, Biochemistry, Genetics and Molecular Biology >> "New Research Directions in DNA Repair", edited by Clark Chen, ISBN 978-953-51-1114-6, Published: May 22, 2013, see Pritchard et al. Nature Reviews | Genetics, May 2012, vol. 13, 358-369).*
Thange et al. Nature Reviews Clinical Oncology, 2011, 8, 587-586.*
International Search Report and Written Opinion for International application No. PCT/US2014/039033 mailed Sep. 23, 2014, completed Sep. 4, 2014.
International Preliminary Report on Patentability for International application No. PCT/US2014/039033 mailed Dec. 3, 2015, issued Nov. 24, 2015.

* cited by examiner

*Primary Examiner* — Nizal Chandrakumar
(74) *Attorney, Agent, or Firm* — Nixon Peabody LLP; Linda B. Huber

(57) ABSTRACT

The invention relates to the identification of genetic signatures and expression profiles that are a part of the Base Excision Repair (BER) pathway, a major DNA repair pathway that modifies base lesions. In one embodiment, the present invention provides a method of determining responsiveness of treatment by BER inhibitors for malignant glioma by determining the presence of a low level of expression of Apex 1, a low level of expression of Apex 2, and a high level of expression of MPG.

10 Claims, 18 Drawing Sheets

Figure 1.

| Gene Name | Expression pattern predicting vulnerability to BER pathway inhibitors |
|---|---|
| MPG | High |
| SMUG1 | No change or high |
| TOPO II | High |
| APEX1 | Low |
| NEIL3 | No change or low |

Figure 6.

| BER pathway member | Function during repair | How will it affect TRC-102 outcome |
|---|---|---|
| MPG | Monofunctional glycosylase which recognizes methylated adducts and generates AP sites | Higher levels of MPG will generate more AP sites which will be available for TRC102 to bind and block repair |
| Smug1 | Monofunctional uracil glycosylase | Higher levels of Smug1 will provide more AP sites for TRC102 to bind |
| Neil3 | Bi-functional glycosylase with AP lyase as well as glycosylase activity. It recognizes and cleaves oxidized bases without generating AP sites | Higher levels of Neil3 will generate fewer AP sites and hence fewer binding sites for TRC102. |
| Apex1 | AP-site specific endonuclease that generates 3'-OH after cleaving the DNA strand 5' to the abasic site | Lower levels of Apex1 is desirable for better outcome with TRC102 treatment. Higher Apex1 in cells will lead to clearance of AP sites. |
| Top II alpha | Generates DNA double strand breaks to relieve torsional stress | TRC102 bound sites are cleaved by Topoisomerase II, which in turn will induce apoptosis. Higher levels of topoisomerase will be indicative of better outcome with TRC102 treatment |

| Prediction | Apex1 | Apex2 | MPG | Smug1 | Top2A | Top2B |
|---|---|---|---|---|---|---|
| Sensitive | 1.353-2.964 | -0.391-0.1154 | 2.77807-1.474 | 3.03843-0.14717 | 4.6441-2.2624 | 4.5769-3.0622 |
| Intermediate | 3.274-3.31 | 0.3002-0.3305 | 1.20077-1.22826 | -0.07986-(-0.05543) | 1.5615-1.3897 | 2.6404-2.6445 |
| Non-responder | 3.608-5.015 | 0.5092-1.5776 | 0.02256-0.94803 | -0.29392-(-1.26883) | -2.7201-0.6554 | 0.6828-2.2145 |

| Prediction | Apex1 | Apex2 | MPG | Smug1 | Top2A | Top2B |
|---|---|---|---|---|---|---|
| Sensitive | -0.988- (-0.283) | -0.839 - (-0.128) | 1.455-0.481 | 1.898-0.441 | 2.259-(-1.25) | 1.367-0.281 |
| Intermediate | -0.076 – (-0.046) | 0.124-0.164 | 0.210-0.176 | 0.136-0.131 | -1.948- (-1.967) | -0.031 – (-0.008) |
| Non-responder | 0.173-1.593 | 0.481 – 1.455 | -1.886- (-0.083) | -0.198- (-1.067) | -2.694- (-5.035) | -0.298- (-1.651) |

| Prediction | Apex1 | Apex2 | MPG | Smug1 | Top2A | Top2B |
|---|---|---|---|---|---|---|
| Sensitive | 472.5-2254.7 | 450.2-798.6 | 3276.9-1007.2 | 1364.1-663.5 | 14608.5-5281.8 | 6607.5-2689.2 |
| Intermediate | 2812.2-3027.3 | 960-1030.9 | 860.3-807.2 | 580.2-564.2 | 4009.9-3608.5 | 2205.9-2068.7 |
| Non-responder | 3446.8-8524.6 | 1190.2-3001.5 | 657.9-255.5 | 461.6-207 | 2443.3-499.5 | 1625.5-319.6 |

| Prediction | Apex1 | Apex2 | MPG | Smug1 | Top2A | Top2B |
|---|---|---|---|---|---|---|
| Sensitive | -1.106-(-0.201) | -1.082-(-0.421) | 1.599-0.522 | 1.390-0.400 | 1.420-(-0.948) | 0.212-(-0.440) |
| Intermediate | 0.045-0.037 | -0.216-(-0.161) | 0.219-0.241 | 0.183-0.151 | -1.277-(-1.292) | -0.746-(-0.708) |
| Non-responder | 0.261-0.959 | 0.134-1.062 | -0.069-(-1.449) | -0.057-(-0.795) | -1.566-(-3.362) | -0.990-(-2.381) |

| Prediction | Apex1 | Apex2 | MPG | Smug1 | Top2A | Top2B |
|---|---|---|---|---|---|---|
| Sensitive | -0.642-(-0.168) | -1.354-(-0.862) | 1.694-0.931 | 2.330-0.849 | 0.468-(-1.311) | 0.146-(-0.635) |
| Intermediate | -0.037-0.010 | -0.634-(-0.639) | 0.623-0.622 | 0.537-0.521 | -2.146-(-2.290) | -0.972-(-0.905) |
| Non-responder | 0.225-0.901 | -0.425-0.053 | 0.366 -(-0.659) | 0.235-(-0.756) | -3.029-(-3.824) | -1.387 -(-2.282) |

GENETIC SIGNATURE OF VULNERABILITY TO INHIBITORS OF BASE EXCISION REPAIR (BER) IN CANCER

CROSS-REFERENCE TO RELATED APPLICATIONS

This application is a National Phase of International Application No. PCT/US14/39033, filed May 21, 2014, currently pending, which designated the U.S. and that International Application was published under PCT Article 21(2) in English. This application includes a claim of priority under 35 U.S.C. 119(e) to U.S. provisional patent application No. 61/825,962, filed May 21, 2013, which is hereby incorporated by reference in its entirety.

FIELD OF THE INVENTION

The invention relates to the medical field, and specifically, to cancer therapeutics and diagnostics.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Malignant glioma is highly aggressive and notoriously resistant to conventional treatments. Temozolomide in combination with radiation is a common treatment regimen for glioma patients. However, due to drug resistance the treatment often fails and the tumor relapses. Enhanced DNA repair capability is one of the main reasons why glioma cells are resistant to DNA damaging agents like temozolomide. Base Excision Repair (BER) is a major DNA repair pathway that modifies base lesions which arise due to alkylation, oxidation, deamination and depurination/depyrimidination of bases.

SUMMARY OF THE INVENTION

Various embodiments include a method of treating a cancer in a subject, comprising obtaining a sample from the subject, assaying the sample to determine the expression levels of Apex 1, Apex 2, and MPG relative to levels found in a non-tumor cell, wherein a low level of Apex 1, a low level of Apex 2, and a high level of MPG relative to levels found in a non-tumor cell is indicative of responsiveness to a cancer therapeutic, and treating the subject. In another embodiment, the cancer therapeutic is an inhibitor of the Base Excision Repair (BER) pathway. In another embodiment, the cancer therapeutic is methoxyamine and/or TRC-102. In another embodiment, the cancer therapeutic is an alkylating agent. In another embodiment, the cancer therapeutic is carboplatin. In another embodiment, the cancer therapeutic is carmustine. In another embodiment, the cancer therapeutic is busulfan, cyclophosphamide, ifosfamide, thiotepa, nitrogen mustardschlorambucil, melphalan, mechlorethamine, nitrosoureascarmustine, lomustine, or streptozocin. In another embodiment, the cancer therapeutic is radiation. In another embodiment, the low level of Apex 1 is between 1.300 and 3.600. In another embodiment, the low level of Apex 1 is between 1.300 and 3.500. In another embodiment, the low level of Apex 1 is between 1.353 and 2.964. In another embodiment, the low level of Apex 2 is between 0 and 0.400. In another embodiment, the low level of Apex 2 is between 0 and 0.3500. In another embodiment, the low level of Apex 2 is between −0.391 and 0.1154. In another embodiment, the high level of MPG is between 1.200 and 2.800. In another embodiment, the high level of MPG is between 1.300 and 2.800. In another embodiment, the high level of MPG is between 1.474 and 2.800. In another embodiment, the cancer is a solid tumor. In another embodiment, the cancer is malignant glioma, breast cancer, colorectal cancer, head and neck cancer and/or lung adenocarcinoma. In another embodiment, the expression levels are determined by microarray analysis.

Other embodiments include a method of treating a cancer in a subject, comprising obtaining a sample, assaying the sample to determine the presence of one or more Base Excision Repair (BER) pathway markers, and treating the subject. In another embodiment, the cancer is a solid tumor. In another embodiment, the solid tumor is malignant glioma, breast cancer, colorectal cancer, head and neck cancer and/or lung adenocarcinoma. In another embodiment, the one or more BER pathway markers include Mpg, Apex1, TopoIIa, Neil3 and/or Smug1. In another embodiment, the one or more BER pathway markers include MBD4, UNG, TDG, OGG, NEIL1, NEIL2 and/or NTH. In another embodiment, the one or more BER pathway markers comprise Apex 1, Apex 2, MPG, Smug 1, Top 2A, and Top 2B. In another embodiment, the one or more BER pathway markers comprise a low level of Apex 1, a low level of Apex 2, a high level of MPG, a high level of Smug 1, a high level of Top 2A, and a high level of Top 2B, relative to levels found in a non-tumor cell. In another embodiment, the one or more BER pathway markers comprise ranges of 1.300 to 3.000 of Apex 1, 0 to 0.200 of Apex 2, 1.400 to 3.000 of MPG, 0.100 to 3.100 of Smug 1, 2.200 to 5.000 of Top 2A, and 3.000 to 4.600 of Top 2B, relative to levels found in a non-tumor cell. In another embodiment, the presence of one or more BER pathway markers are determined by microarray analysis. In another embodiment, treating the subject comprises administering a therapeutically effective dosage of an alkylating agent.

Other embodiments include a method of diagnosing a cancer in a subject, comprising obtaining a sample, assaying the sample to determine the presence or absence of one or more Base Excision Repair (BER) pathway markers, and diagnosing the disease based on the presence of one or more BER pathway markers in the subject. In another embodiment, the presence of one or more BER pathway markers comprises a low level of Apex 1, a low level of Apex 2, and a high level of MPG, relative to levels found in a non-tumor cell. In another embodiment, the cancer is a malignant glioma. In another embodiment, the cancer is sensitive to temozolomide treatment. In another embodiment, the one or more BER pathway markers comprise Apex 1, Apex 2, MPG, Smug 1, Top 2A, and Top 2B. In another embodiment, the one or more BER pathway markers comprise a low level of Apex 1, a low level of Apex 2, a high level of MPG, a high level of Smug 1, a high level of Top 2A, and a high level of Top 2B, relative to levels found in a non-tumor cell. In another embodiment, the presence of one or more BER pathway markers are determined by microarray analysis.

Various embodiments include a method treating a subject, comprising determining the presence of a pattern of Base Excision Repair (BER) pathway markers, identifying one or more inhibitors to one of the BER genes that would benefit the patient based on the pattern, and administering a therapeutically effective dosage of the one or more inhibitors to the subject. In another embodiment, the pattern of BER pathway markers includes determining the presence of gene expression and/or protein abundance from genes involved in BER. In another embodiment, the one or more inhibitors include alkylating agents.

Various embodiments include a kit, comprising a panel of one or more Base Excision Repair (BER) pathway markers. In another embodiment, the one or more BER pathway markers includes Mpg, Apex1, TopoIIa, Neil3 and/or Smug1. In another embodiment, the one or more BER pathway markers include MBD4, UNG, TDG, OGG, NEIL1, NEIL2 and/or NTH. In another embodiment, the one or more BER pathway markers comprises a low level of Apex 1, a low level of Apex 2, and a high level of MPG relative to levels found in a non-tumor cell.

Other embodiments include a method of drug discovery, comprising determining the presence of a pattern of gene expression and/or protein abundance from one or more genes involved in Base Excision Repair (BER), and preparing one or more suitable inhibitors of BER genes based on the pattern of gene expression and/or protein abundance. In another embodiment, the one or more suitable inhibitors are alkylating agents.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 1 depicts, in accordance with an embodiment herein, five gene signature for TRC 102 and TMZ combination treatment. Since in different tissues other glycosylases might be dominant for other solid tumors, the 5 gene signature may be expanded to 12 gene signature by including other glycosylases (MBD4, UNG, TDG, OGG, NEIL1, NEIL2 and NTH).

FIG. 6 depicts, in accordance with an embodiment herein, five BER pathway genes critical for response to TRC-102 and Temozolomide treatment. TCGA database query: All five genes show upregulation in tumor vs non-tumor control. MPG and Apex1 are both upregulated in glioma tumors.

DESCRIPTION OF THE INVENTION

Figure 2:
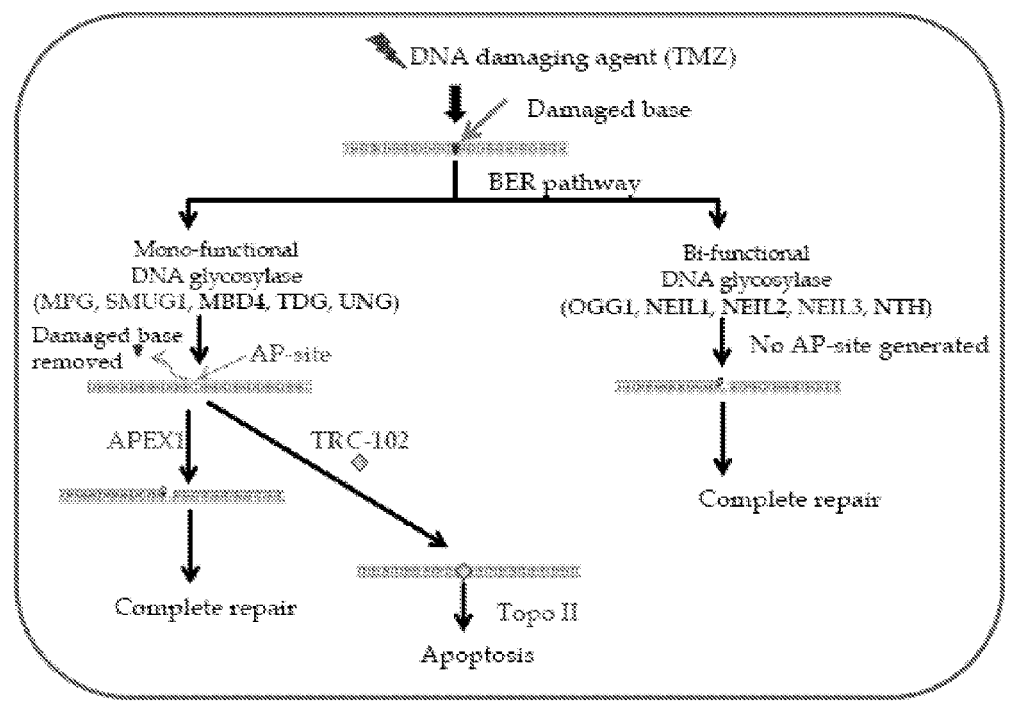
FIG. 2 depicts, in accordance with an embodiment herein, BER pathway and TRC-102. DNA lesions generated by temozolomide are predominantly repaired through the base excision repair (BER) pathway. An important first step in the pathway is the recognition of the lesion by DNA glycosylases. The damaged base could be processed by monofunctional or bifunctional glycosylases. Monofunctional glycosylase flips the damaged base out of the double helix leaving an exposed AP site. This AP site is recognized and cleaved by the endonuclease APEX1 giving rise to a 3' hydroxyl adjacent to a 5' deoxyribosephosphate. The single strand break is then recognized and repaired by rest of the BER pathway machinery (PNKP, DNA pol b, Fen1, Xrcc1). TRC-102 binds exposed AP sites and blocks further repair by the BER pathway enzymes. This aberrant structure is recognized by Topoisomarease II which cleaves the DNA and generates double strand break which eventually triggers apoptosis. If the repair proceeds in presence of a bifunctional glycosylases no AP sites are generated since they possess both glycosylase as well as lyase activity.
Figure 3:
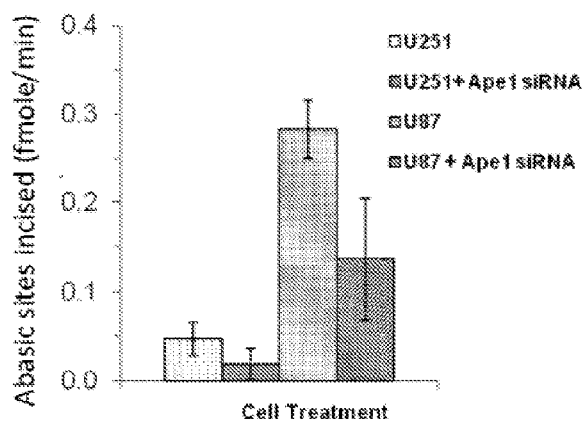
FIG. 3 depicts, in accordance with an embodiment herein, decreased Apex1 leads to decreased removal or clearance of AP-sites. Apex1 overexpressing cell line when treated with Apex1 siRNA to knockdown its expression shows decrease in removal or excision of Abasic (AP) sites (Naidu M et al., J. Radiat. Res. 2010).
Figure 4:
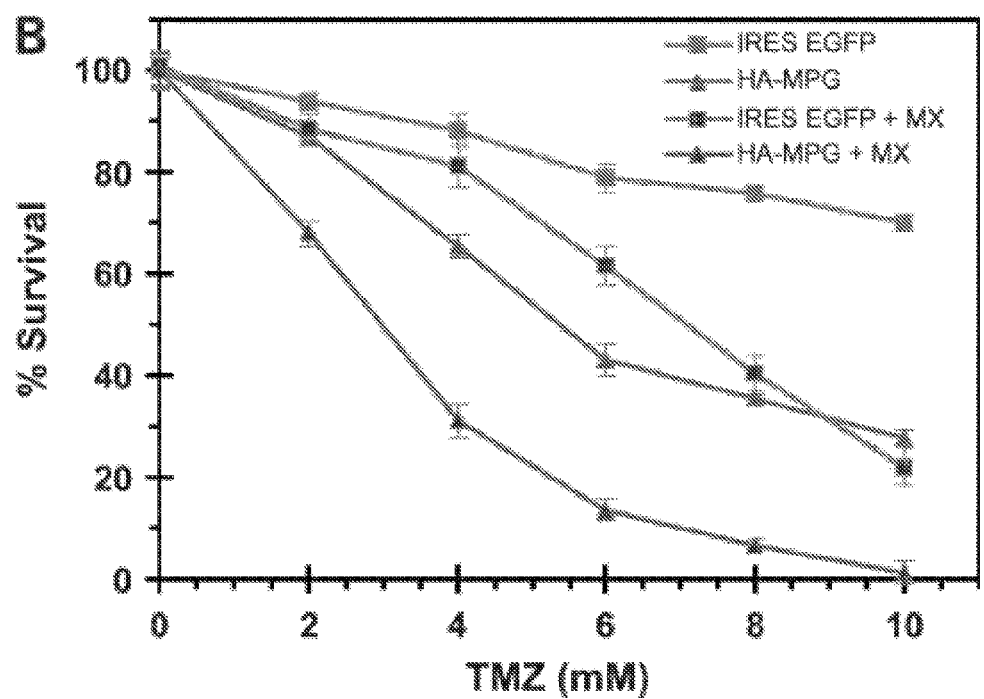
FIG. 4 depicts, in accordance with an embodiment herein, overexpression of MPG leads to accumulation of AP sites and sensitizes cells to TMZ. Breast cancer cells were transduced with adenovirus overexpressing MPG and treated with methoxyamine (TRC 102) and TMZ (Rinne M et al., Mol Cancer Ther. 2004).
Figure 5:
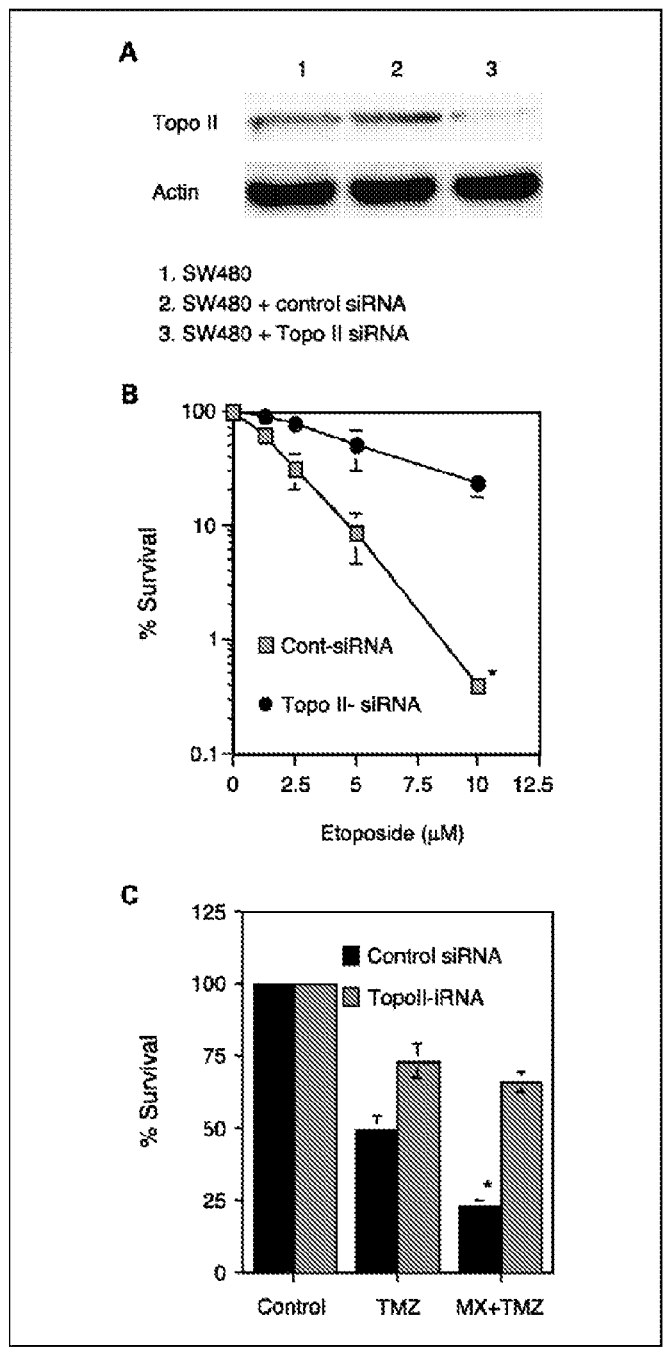
FIG. 5 depicts, in accordance with an embodiment herein, decreased Topo II expression leads to increased resistance to cytotoxic drugs (Yan L et al., Clin. Cancer Res. 2007).
Figure 7:
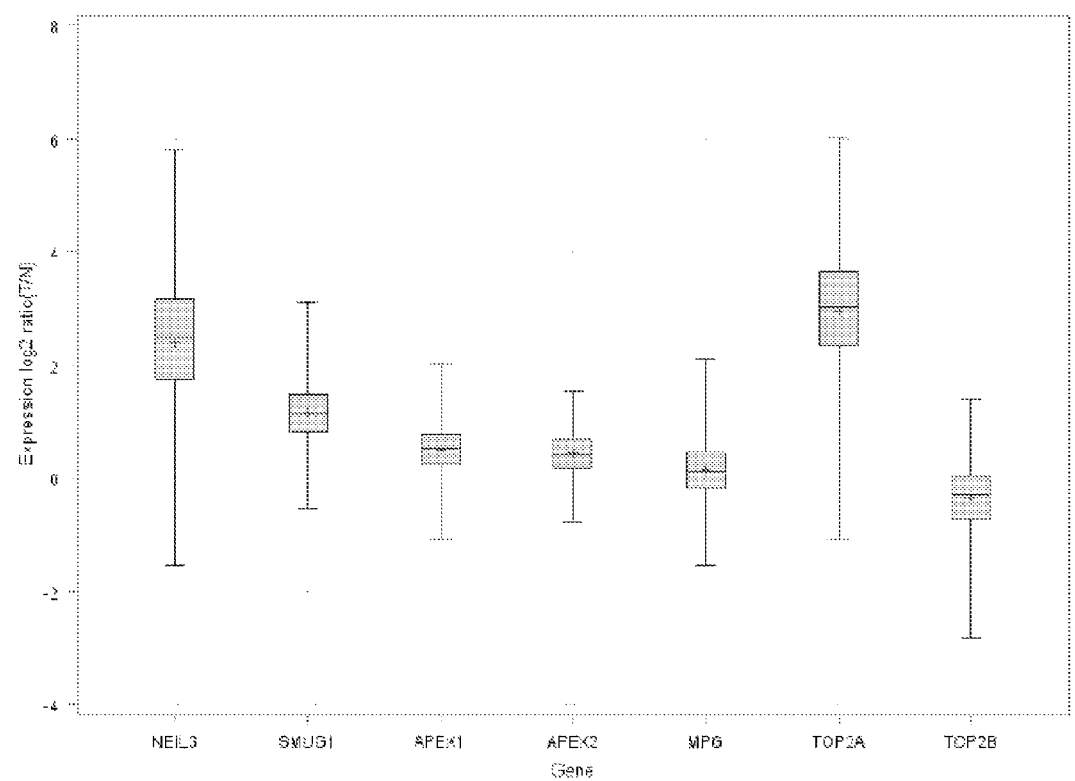
FIG. 7 depicts, in accordance with an embodiment herein, Box plot for BER genes. Box Plots of normalized gene expression measurements of BER pathway genes in glioma tissue as compared to non-tumor tissue.
Figure 8:
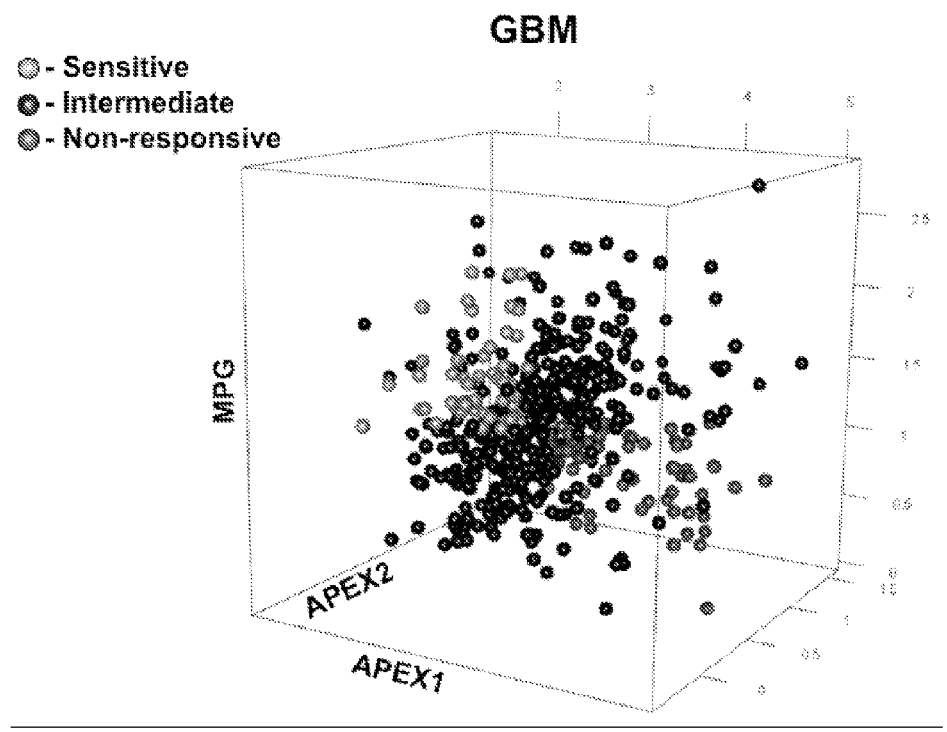
FIG. 8 depicts, in accordance with an embodiment herein, a box plot of three key BER signature genes Apex1, Apex2 and MPG. Box plots of normalized gene expression measurements of BER pathway genes in glioma tissue as compared to non-tumor tissue.
Figure 9:
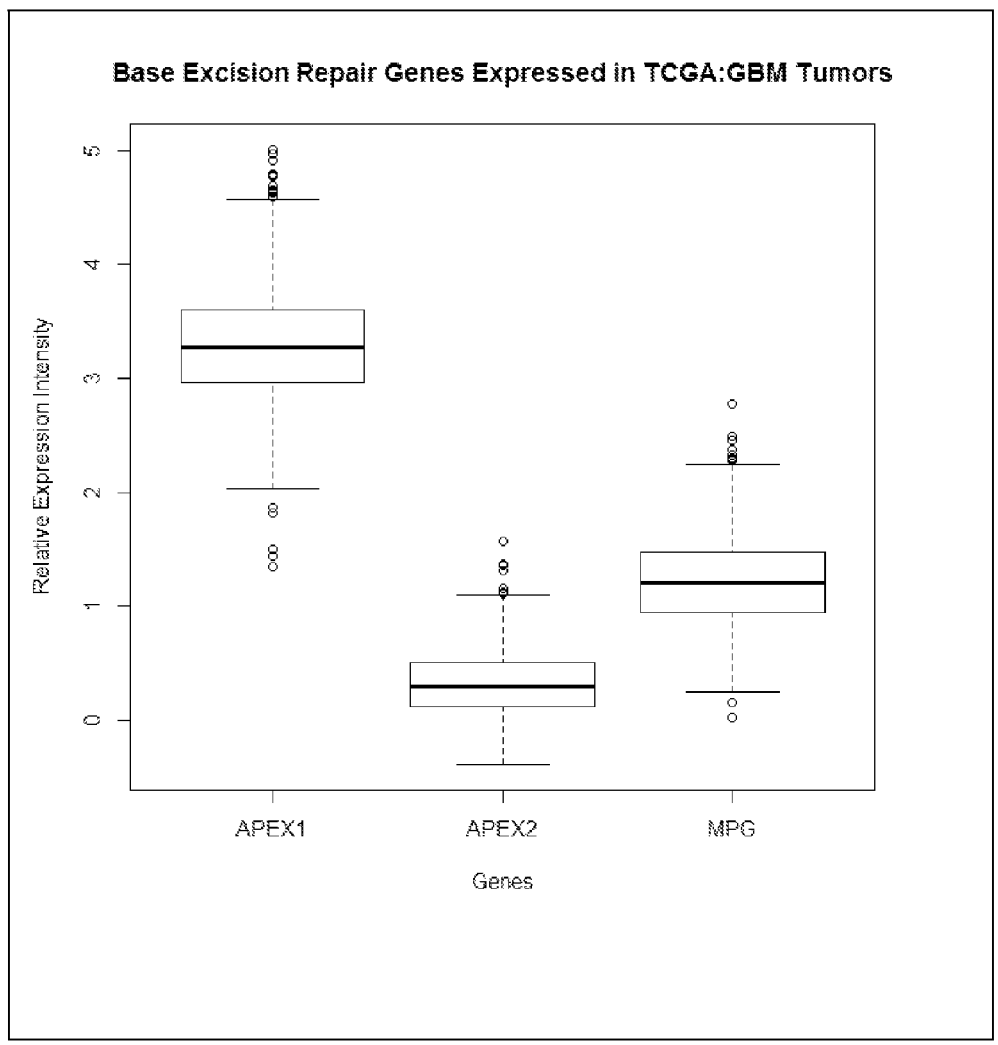
FIG. 9 depicts, in accordance with an embodiment herein, 3D-scatter plot of the correlative expression of MPG, Apex1 and Apex2 genes across TCGA glioblastoma database. Tumors in accordance with the gene signature are predicted to be sensitive to TMZ and TRC102 treatment are labeled in green, tumors with intermediate levels of MPG and Apex1/2 are labeled in black while the non-responder group with high levels of Apex1/2 and low MPG are labeled red.
Figures 10, 11:
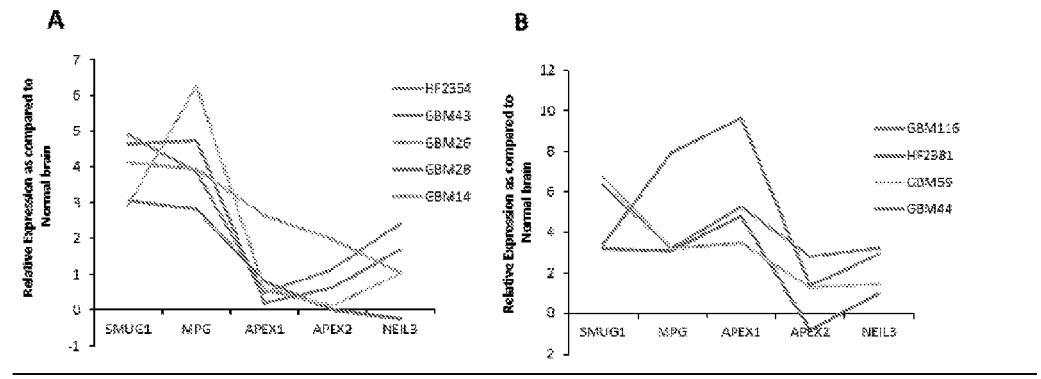
FIG. 10 depicts, in accordance with an embodiment herein, predicted expression ranges using microarray gene expression analysis for glioblastoma tumors. The range of expression of BER pathway genes can predict if the tumor will classify as sensitive to TRC102 and TMZ, intermediate responder or non-responder. Importantly, vulnerability prediction is shown to work when values for all three genes, Apex1, Apex2 and MPG, are within the specified range.
FIG. 11 depicts, in accordance with an embodiment herein, real-time PCR analysis of BER pathway genes in patient-derived xenograft tumors. Panel A shows tumors which depict the predicted gene signature (high MPG, Smug1 and low Apex1/2, Neil3) while panel B shows predicted non-responders.
Figure 12:
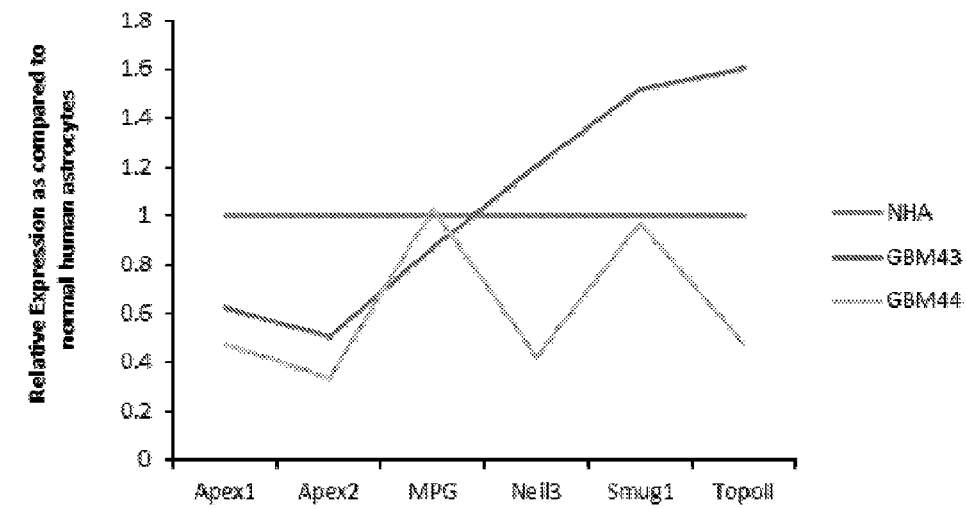
FIG. 12 depicts, in accordance with an embodiment herein, real-time PCR analysis of BER pathway genes in glioma stem/initiating cells derived from the one of the responder (GBM43) as well as non-responder lines (GBM44).
Figure 13:
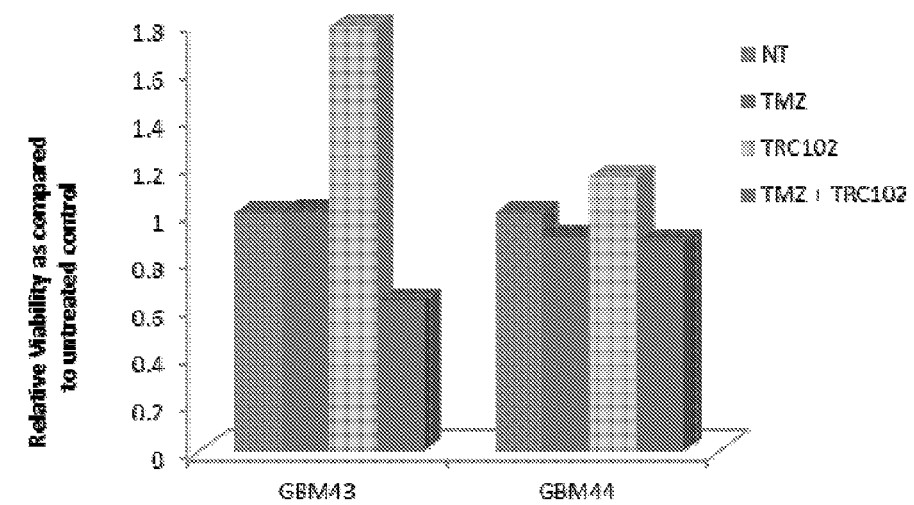
FIG. 13 depicts, in accordance with an embodiment herein, cell viability in predicted responder (GBM43) and non-responder (GBM44) GBM lines after treatment with TRC102 and TMZ. GBM43 is sensitive to the combination treatment of TRC102 and TMZ while GBM44 is resistant as predicted.
Figure 14:
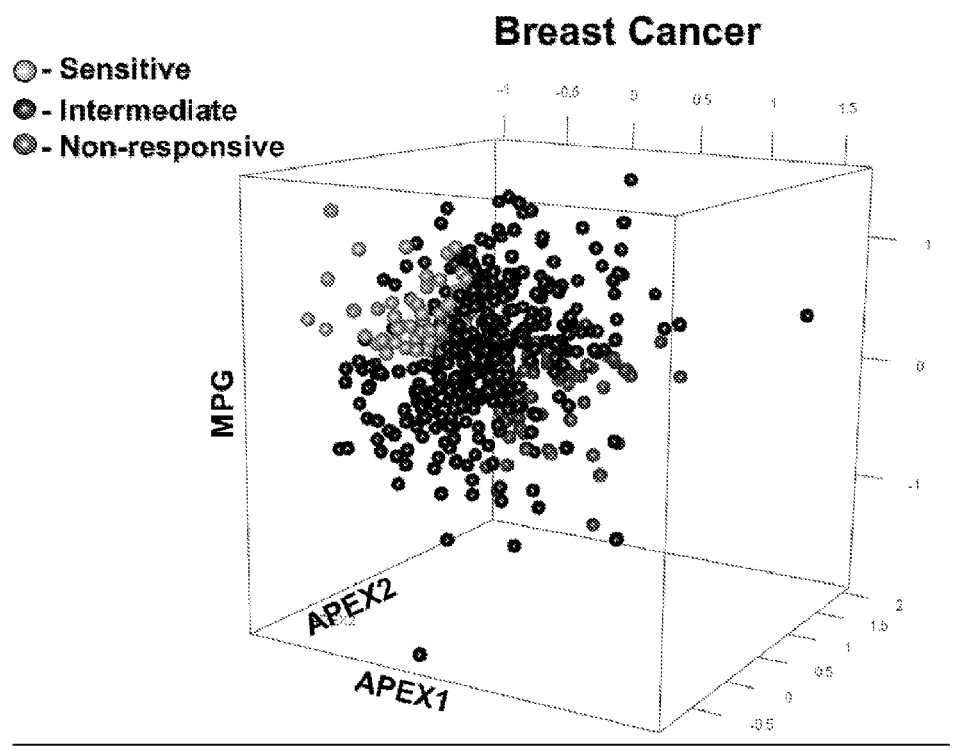
FIG. 14 depicts, in accordance with an embodiment herein, 3D-scatter plot of the correlative expression of MPG, Apex1 and Apex2 genes across TCGA breast cancer database. Tumors in accordance with the gene signature are predicted to be sensitive to TMZ and TRC102 treatment are labeled in green, tumors with intermediate levels of MPG and Apex1/2 are labeled in black while the non-responder group with high levels of Apex1/2 and low MPG are labeled red.
Figures 15, 16:
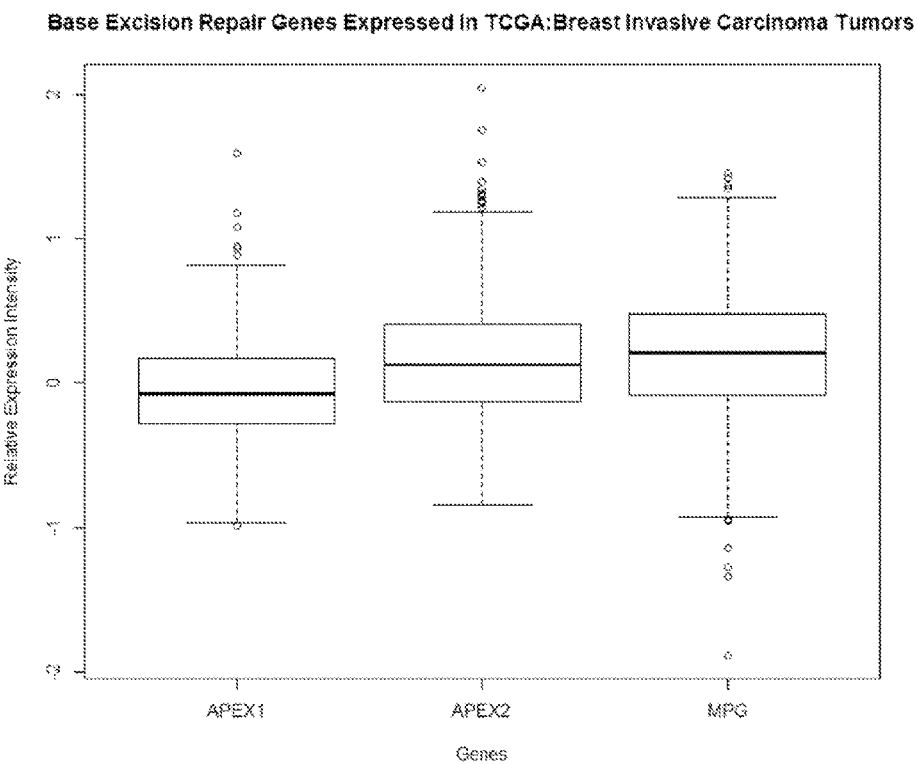
FIG. 15 depicts, in accordance with an embodiment herein, a box plot of three key BER signature genes Apex1, Apex2 and MPG. Box plots of normalized gene expression measurements of BER pathway genes in breast invasive carcinoma tissue as compared to non-tumor tissue.
FIG. 16 depicts, in accordance with an embodiment herein, predicted expression ranges using microarray gene expression analysis for breast invasive carcinoma tumors. The range of expression of BER pathway genes can predict if the tumor will classify as sensitive to TRC102 and TMZ, intermediate responder or non-responder. Importantly, vulnerability prediction is shown to work when values for all three genes, Apex1, Apex2 and MPG, are within the specified range.
Figure 17:
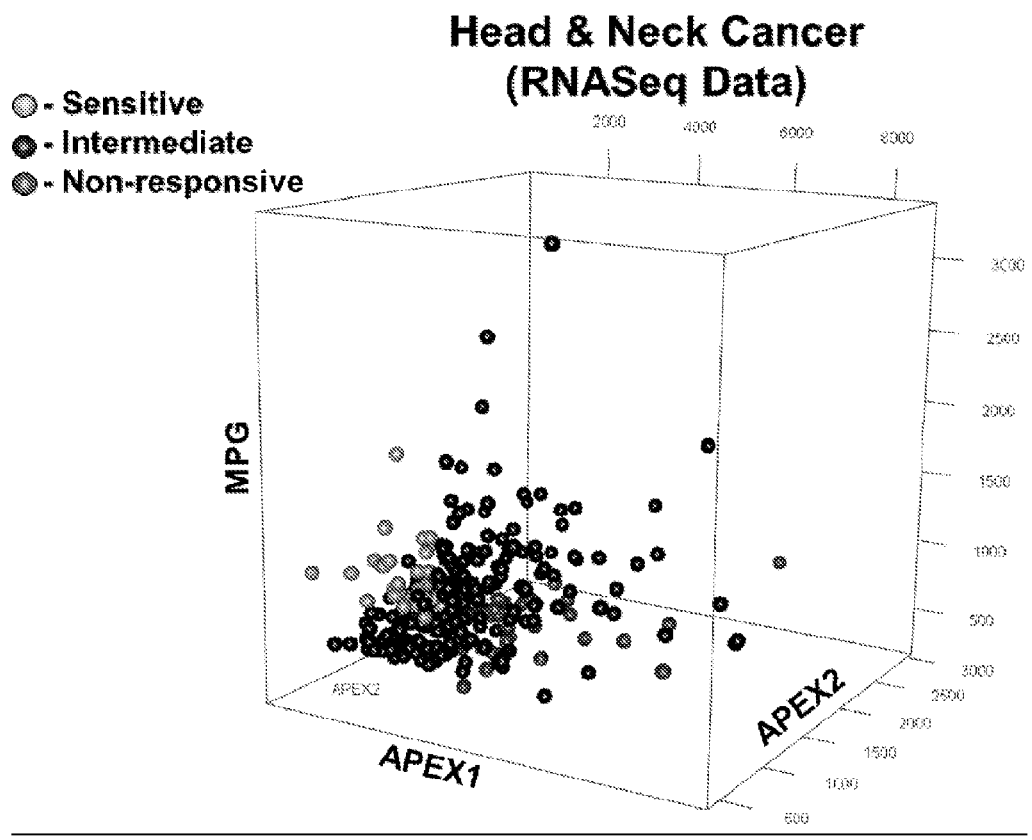
FIG. 17 depicts, in accordance with an embodiment herein, 3D-scatter plot of the correlative expression of MPG, Apex1 and Apex2 genes across TCGA Head and Neck cancer database. Tumors in accordance with the gene signature are predicted to be sensitive to TMZ and TRC102 treatment are labeled in green, tumors with intermediate levels of MPG and Apex1/2 are labeled in black while the non-responder group with high levels of Apex1/2 and low MPG are labeled red.
Figure 18:
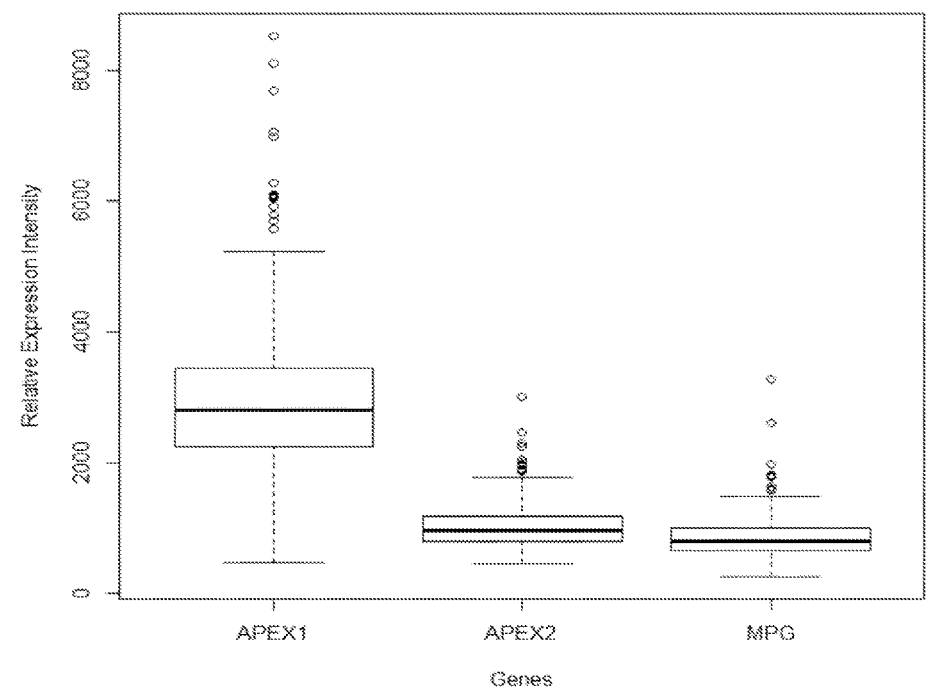
FIG. 18 depicts, in accordance with an embodiment herein, a box plot of three key BER signature genes Apex1, Apex2 and MPG. Box plots of normalized gene expression measurements of BER pathway genes in head and neck cancer tissue as compared to non-tumor tissue.
Figures 19, 20:
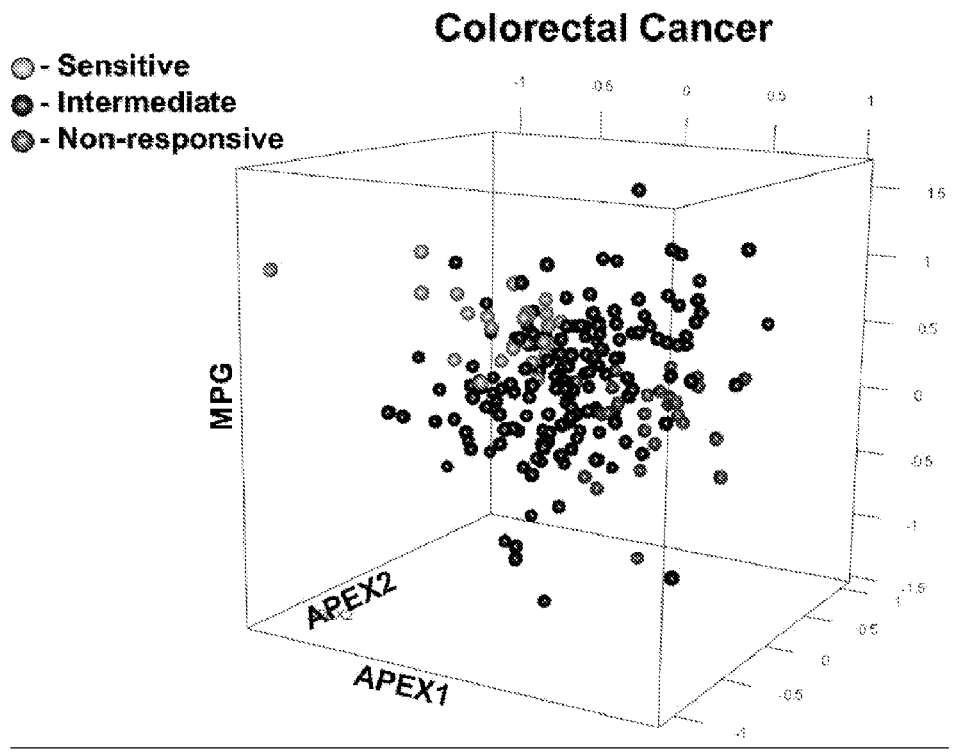
FIG. 19 depicts, in accordance with an embodiment herein, predicted expression ranges using RNA-seq analysis for head and neck tumors. The range of expression of BER pathway genes can predict if the tumor will classify as sensitive to TRC102 and TMZ, intermediate responder or non-responder. Importantly, vulnerability prediction is shown to work when values for all three genes, Apex1, Apex2 and MPG, are within the specified range.
FIG. 20 depicts, in accordance with an embodiment herein, 3D-scatter plot of the correlative expression of MPG, Apex1 and Apex2 genes across TCGA colorectal cancer database. Tumors in accordance with the gene signature are predicted to be sensitive to TMZ and TRC102 treatment are labeled in green, tumors with intermediate levels of MPG and Apex1/2 are labeled in black while the non-responder group with high levels of Apex1/2 and low MPG are labeled red.
Figure 21:
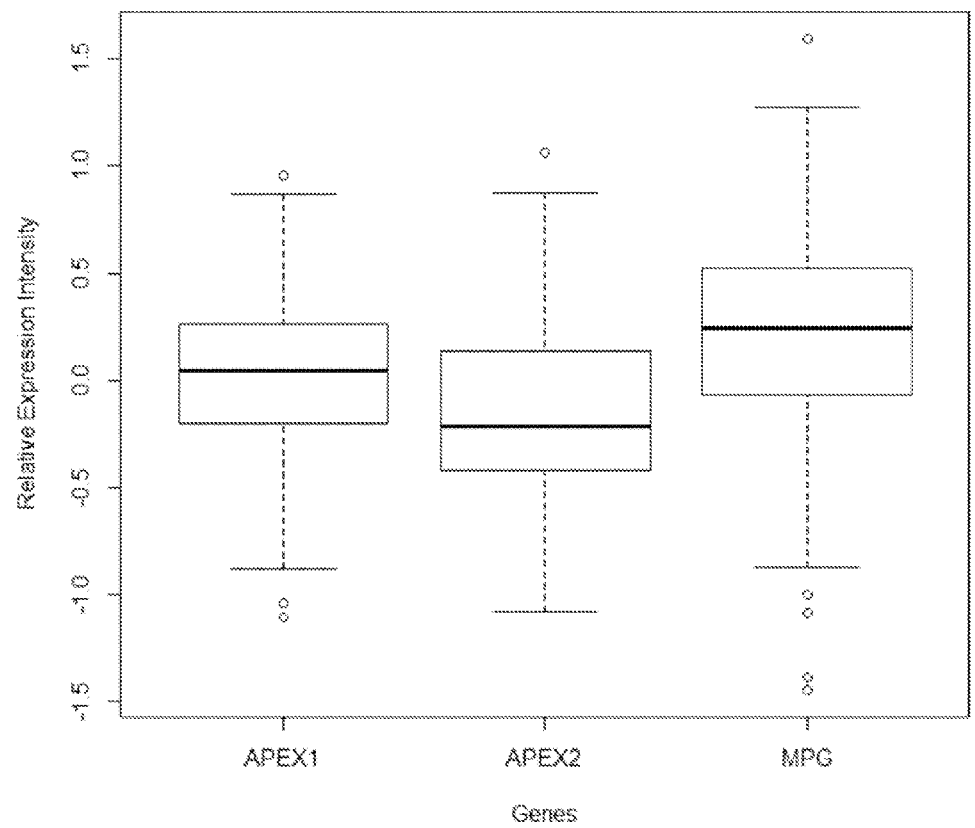
FIG. 21 depicts, in accordance with an embodiment herein, a box plot of three key BER signature genes Apex1, Apex2 and MPG. Box plots of normalized gene expression measurements of BER pathway genes in colorectal cancer tissue as compared to non-tumor tissue.
Figures 22, 23:
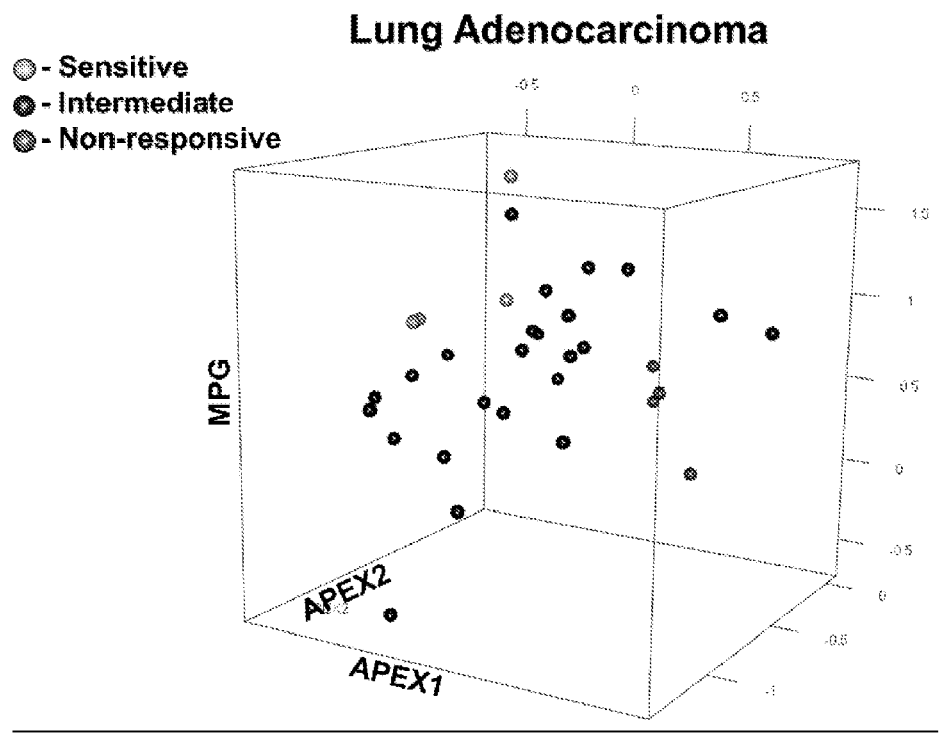
FIG. 22 depicts, in accordance with an embodiment herein, predicted expression ranges using microarray gene expression analysis for colorectal tumors. The range of expression of BER pathway genes can predict if the tumor will classify as sensitive to TRC102 and TMZ, intermediate responder or non-responder. Importantly, vulnerability prediction is shown to work when values for all three genes, Apex1, Apex2 and MPG, are within the specified range.
FIG. 23 depicts, in accordance with an embodiment herein, 3D-scatter plot of the correlative expression of MPG, Apex1 and Apex2 genes across TCGA lung adenocarcinoma database. Tumors in accordance with the gene signature are predicted to be sensitive to TMZ and TRC102 treatment are labeled in green, tumors with intermediate levels of MPG and Apex1/2 are labeled in black while the non-responder group with high levels of Apex1/2 and low MPG are labeled red.
Figures 24, 25:
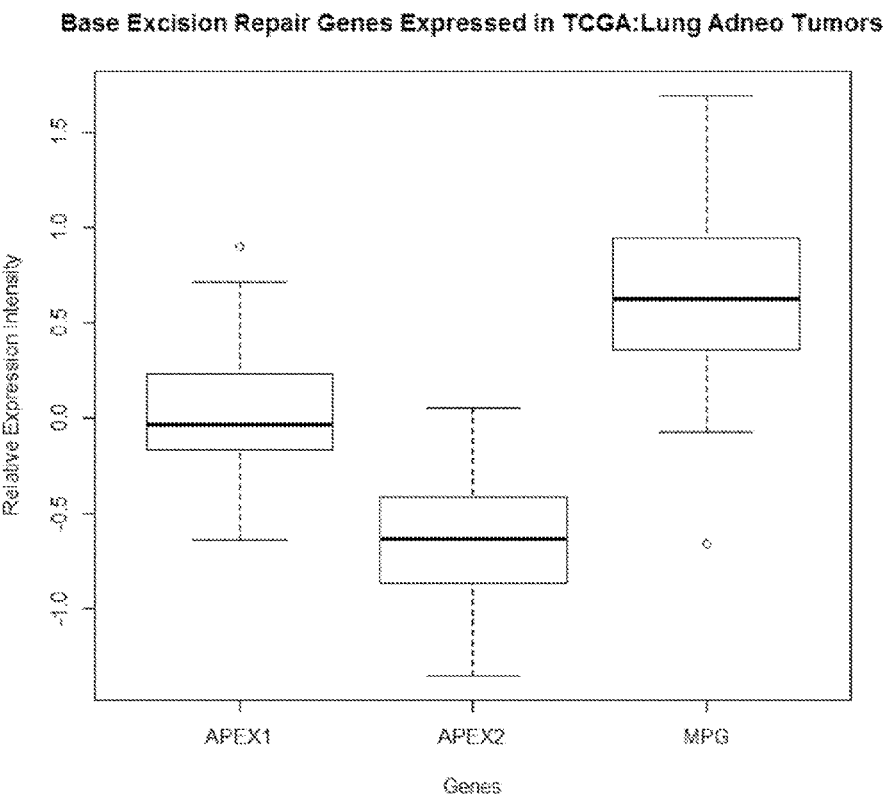
FIG. 24 depicts, in accordance with an embodiment herein, a box plot of three key BER signature genes Apex1, Apex2 and MPG. Box plots of normalized gene expression measurements of BER pathway genes in lung adenocarcinoma tissue as compared to non-tumor tissue.
FIG. 25 depicts, predicted expression ranges using microarray gene expression analysis for lung adenocarcinoma tumors. The range of expression of BER pathway genes can predict if the tumor will classify as sensitive to TRC102 and TMZ, intermediate responder or non-responder. Importantly, vulnerability prediction is shown to work when values for all three genes, Apex1, Apex2 and MPG, are within the specified range.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As disclosed herein, enhanced DNA repair capability is one of the main reasons why glioma cells are resistant to DNA damaging agents like temozolomide. Base Excision Repair (BER) is a major DNA repair pathway that modifies base lesions which arise due to alkylation, oxidation, deamination and depurination/depyrimidination of bases. TRC-102 or Methoxyamine is a potent inhibitor of BER pathway. It binds abasic sites and disrupts BER pathway. However, effective TRC102 requires that the cells express high levels of monofunctional glycosylases to generate abasic sites and low levels of endonuclease which will repair and remove the abasic site. Based on the analysis of expression profiles of 428 glioma samples from TCGA database, the inventors have identified a 5 gene signature (Mpg, Apex1, TopoIIa, Neil3 and Smug1) to predict the outcome of TRC-102 and TMZ treatment in glioma patients.

In one embodiment, the present invention provides a method of treating cancer in a subject by obtaining a sample, assaying the sample to determine the presence of one or more BER pathway markers, and treating the subject. In another embodiment, the cancer is malignant glioma. In another embodiment, the one or more BER pathway markers include Mpg, Apex1, TopoIIa, Neil3 and/or Smug1. In another embodiment, the one or more BER pathway markers include MBD4, UNG, TDG, OGG, NEIL1, NEIL2 and/or NTH. In another embodiment, the one or more BER pathway markers includes the presence of a high level of monfunctional glycosylases and/or low levels of endonucleases. In another embodiment, the one or more BER pathway markers comprise a low level of Apex 1, a low level of Apex 2, and a high level of MPG relative to levels found in a non-tumor cell. In another embodiment, the one or more BER BER pathway markers comprise a low level of Apex 1, a low level of Apex 2, a high level of MPG, a high level of Smug 1, a high level of Top 2A, and a high level of Top 2B, relative to levels found in a non-tumor cell. In another embodiment, the one or more BER pathway markers comprise ranges of 1.300 to 3.000 of Apex 1, 0 to 0.200 of Apex 2, 1.400 to 3.000 of MPG, 0.100 to 3.100 of Smug 1, 2.200 to 5.000 of Top 2A, and 3.000 to 4.600 of Top 2B, relative to levels found in a non-tumor cell. In another embodiment, treating the subject comprises administering a therapeutically effective dosage of a DNA damaging agent. In another embodiment, treating the subject comprises administering a therapeutically effective dosage of temozolomide. In another embodiment, treating the subject comprises administering a therapeutically effective dosage of TRC-102 and/or Methoxyamine.

In one embodiment, the present invention provides a method of diagnosing a disease in a subject, by obtaining a sample, assaying the sample to determine the presence of one or more BER pathway markers, and diagnosing the disease based on the presence of one or more BER pathway markers. In another embodiment, the one or more BER pathway markers comprise a low level of Apex 1, a low level of Apex 2, and a high level of MPG relative to levels found in a non-tumor cell. In another embodiment, the one or more BER BER pathway markers comprise a low level of Apex 1, a low level of Apex 2, a high level of MPG, a high level of Smug 1, a high level of Top 2A, and a high level of Top 2B, relative to levels found in a non-tumor cell. In another embodiment, the one or more BER pathway markers comprise ranges of 1.300 to 3.000 of Apex 1, 0 to 0.200 of Apex 2, 1.400 to 3.000 of MPG, 0.100 to 3.100 of Smug 1, 2.200 to 5.000 of Top 2A, and 3.000 to 4.600 of Top 2B, relative to levels found in a non-tumor cell. In another embodiment, the presence of one or more BER pathway markers are detected using qPCR, microarray, RNA-seq, and/or Mass-spectrometry.

In another embodiment, the present invention provides a method of treating a disease in a subject by diagnosing the subject, and then administering a therapeutically effective dosage of an inhibitor of one or more BER genes. In another embodiment, the present invention provides a method by which a pattern of gene expression or protein abundance from specific genes involved in base excision repair (BER) determines that an inhibitor to one of the BER genes will benefit the patient. In another embodiment, the present invention provides a method by which a pattern of gene expression or protein abundance from specific genes involved in base excision repair (BER) determines that an inhibitor to more than one of the BER genes will benefit the patient. In another embodiment, the present invention provides a method by which a pattern of gene expression or protein abundance from specific genes involved in base excision repair (BER) determines that an inhibitor to one of the BER genes will not benefit the patient. In another embodiment, the one or more BER pathway markers include Mpg, Apex1, TopoIIa, Neil3 and/or Smug1. In another embodiment, the one or more BER pathway markers include MBD4, UNG, TDG, OGG, NEIL1, NEIL2 and/or NTH. In another embodiment, the one or more BER pathway markers comprise a low level of Apex 1, a low level of Apex 2, and a high level of MPG relative to levels found in a non-tumor cell. In another embodiment, the one or more BER BER pathway markers comprise a low level of Apex 1, a low level of Apex 2, a high level of MPG, a high level of Smug 1, a high level of Top 2A, and a high level of Top 2B, relative to levels found in a non-tumor cell. In another embodiment, the one or more BER pathway markers comprise ranges of 1.300 to 3.000 of Apex 1, 0 to 0.200 of Apex 2, 1.400 to 3.000 of MPG, 0.100 to 3.100 of Smug 1, 2.200 to 5.000 of Top 2A, and 3.000 to 4.600 of Top 2B, relative to levels found in a non-tumor cell.

In one embodiment, the present invention provides a method by which a pattern of elevated gene expression or protein abundance from specific genes involved in base excision repair (BER) reveals specific alternative genes or gene products in the BER process, the inhibition of which would benefit the patient. In another embodiment, the genes and/or gene products in the BER pathway enables drug discovery and development. In another embodiment, the one or more BER pathway markers include Mpg, Apex1, TopoIIa, Neil3 and/or Smug1. In another embodiment, the one or more BER pathway markers include MBD4, UNG, TDG, OGG, NEIL1, NEIL2 and/or NTH. In another embodiment, the one or more BER pathway markers comprise a low level of Apex 1, a low level of Apex 2, and a high level of MPG relative to levels found in a non-tumor cell. In another embodiment, the one or more BER BER pathway markers comprise a low level of Apex 1, a low level of Apex 2, a high level of MPG, a high level of Smug 1, a high level of Top 2A, and a high level of Top 2B, relative to levels found in a non-tumor cell. In another embodiment, the one or more BER pathway markers comprise ranges of 1.300 to 3.000 of Apex 1, 0 to 0.200 of Apex 2, 1.400 to 3.000 of MPG, 0.100 to 3.100 of Smug 1, 2.200 to 5.000 of Top 2A, and 3.000 to 4.600 of Top 2B, relative to levels found in a non-tumor cell.

In one embodiment, the present invention provides a method by which a pattern of low gene expression or diminished protein abundance from specific genes involved in base excision repair (BER) reveals specific alternative genes or gene products the inhibition of which would set the stage for elevating the abundance of critical protein (gene product) that alters the vulnerability of a disease to a BER inhibitor. In another embodiment, the findings may be used for additional drug discovery and/or development.

There are many techniques readily available in the field for detecting the presence or absence of polypeptides or other biomarkers, including protein microarrays. For example, some of the detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Similarly, there are any number of techniques that may be employed to isolate and/or fractionate biomarkers. For example, a biomarker may be captured using biospecific capture reagents, such as antibodies, aptamers or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer and hybrids of these.

Alternatively, for example, the presence of biomarkers such as polypeptides maybe detected using traditional immunoassay techniques. Immunoassay requires biospecific capture reagents, such as antibodies, to capture the analytes. The assay may also be designed to specifically distinguish protein and modified forms of protein, which can be done by employing a sandwich assay in which one antibody captures more than one form and second, distinctly labeled antibodies, specifically bind, and provide distinct detection of, the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, biomarkers may also be fractionated to isolate them from other components in a solution or of blood that may interfere with detection. Fractionation may include platelet isolation from other blood components, sub-cellular fractionation of platelet components and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Overview

Malignant glioma is highly aggressive and notoriously resistant to conventional treatments. Temozolomide in combination with radiation is one of the most common treatment regimens for glioma patients. However, due to drug resistance the treatment fails and tumor relapses. Enhanced DNA repair capability is one of the main reasons why glioma cells are resistant to DNA damaging agents like temozolomide. Base Excision Repair (BER) is the major DNA repair pathway that modifies base lesions which arise due to alkylation, oxidation, deamination and depurination/depyrimidination of bases. TRC-102 or Methoxyamine is a potent inhibitor of BER pathway. It binds abasic sites and disrupts BER pathway. However, effective TRC102 requires that the cells express high levels of monofunctional glycosylases to generate abasic sites and low levels of endonuclease which will repair and remove the abasic site. Based on the analysis of expression profiles of 428 glioma samples from TCGA database, the inventors have identified a 5 gene signature (Mpg, Apex1, TopoIIa, Neil3 and Smug1) to predict the outcome of TR-102 and TMZ treatment in glioma patients.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of treating a cancer in a subject, comprising:
    obtaining a sample from the subject;
    assaying the sample to determine the expression levels of Base Excision Repair (BER) pathway markers comprising Apex 1, Apex 2, and MPG relative to levels found in a non-tumor cell,
        wherein a low level of Apex 1, a low level of Apex 2, and a high level of MPG relative to levels found in a non-tumor cell is indicative of responsiveness to a cancer therapeutic; and
    treating the subject when a low level of Apex 1, a low level of Apex 2, and a high level of MPG is found,
    wherein the low level of Apex 1 is between 1.300 and 3.600, the low level of Apex 2 is between 0 and 0.400 and the high level of MPG is between 1.200 and 2.800.

2. The method of claim 1, wherein the cancer therapeutic is an inhibitor of the Base Excision Repair (BER) pathway.

3. The method of claim 1, wherein the cancer therapeutic is methoxyamine (TRC-102), and Temozolomide (TMZ).

4. The method of claim 1, wherein the low level of Apex 2 is between −0.391 and 0.1154.

5. The method of claim 1, wherein the cancer is a solid tumor.

6. The method of claim 1, wherein the cancer is malignant glioma, breast cancer, colorectal cancer, head and neck cancer and/or lung adenocarcinoma.

7. The method of claim 1, wherein the expression levels are determined by microarray analysis.

8. The method of claim 1, wherein the one or more BER pathway markers further comprise TopoIIa, Neil3, Smug1, MBD4, UNG, TDG, OGG, NEIL1, NEIL2, NTH, Top 2A, and/or Top 2B.

9. The method of claim 8, wherein the low level of Apex 1, the low level of Apex 2, the high level of MPG, a high level of Smug 1, a high level of Top 2A, and a high level of Top 2B, relative to levels found in a non-tumor cell are indicative of responsiveness to a cancer therapeutic.

10. The method of claim 9, wherein ranges of 0.100 to 3.100 of Smug 1, 2.200 to 5.000 of Top 2A, and 3.000 to 4.600 of Top 2B, relative to levels found in a non-tumor cell are further indicative of responsiveness to a cancer therapeutic.

* * * * *